US010542679B2

(12) United States Patent
Younk et al.

(10) Patent No.: US 10,542,679 B2
(45) Date of Patent: Jan. 28, 2020

(54) DEVICE AND METHOD FOR TRACKING AND MARKING BALED FORAGE MATERIAL

(71) Applicant: Animal Health International, Inc., Greeley, CO (US)

(72) Inventors: Bill Younk, Greeley, CO (US); Wes Byers, Ocala, FL (US)

(73) Assignee: ANIMAL HEALTH INTERNATIONAL, INC., Greeley, CO (US)

( * ) Notice: Subject to any disclaimer, the term of this patent is extended or adjusted under 35 U.S.C. 154(b) by 220 days.

(21) Appl. No.: 15/784,932

(22) Filed: Oct. 16, 2017

(65) Prior Publication Data

US 2018/0084730 A1  Mar. 29, 2018

Related U.S. Application Data

(63) Continuation-in-part of application No. 14/667,494, filed on Mar. 24, 2015, now Pat. No. 9,986,690.

(51) Int. Cl.
*A01F 15/08* (2006.01)
*G01N 33/00* (2006.01)
(Continued)

(52) U.S. Cl.
CPC .......... *A01F 15/08* (2013.01); *A01F 15/0816* (2013.01); *A01F 15/0825* (2013.01);
(Continued)

(58) Field of Classification Search
CPC ........ A01F 15/00; A01F 15/042; A01F 15/08; A01F 15/0858; A01F 15/10; A01F 15/14;
(Continued)

(56) References Cited

U.S. PATENT DOCUMENTS 3,474,937 A  10/1969  Frey
3,722,934 A   3/1973  Nolt et al.
(Continued)

FOREIGN PATENT DOCUMENTS

CA    682474 A   3/1964
CA   1045446 A   1/1979
(Continued)

OTHER PUBLICATIONS

Ferguson, "The industry's leading baler leads the way again", HESSTON, 2014, 26 pages.
(Continued)

*Primary Examiner* — Jimmy T Nguyen
(74) *Attorney, Agent, or Firm* — Berg Hill Greenleaf Ruscitti LLP.

(57) ABSTRACT

A device and method for tracking and marking bailed forage material is provided. Predetermined parameters are measured as the forage material enters the intake of a processing machine and prior to the forage material being transferred to a baling chamber of the machine. As the forage material passes through the machine, the locations of discrete portions or flakes of the forage material are linearly tracked so that each portion may receive pre-selected markings indicative of measured parameters of each portion. A plurality of sensor stations is incorporated within the machine to track the locations of the portions of material. After the forage material is baled, a marking station generates markings applied to each bale which corresponds to the measured parameters for the corresponding discrete portions. Observed parameters may include moisture content, volume, density, temperature, nutritional content, an amount and type of conditioning inoculant applied to each flake, among others. Multiple markings can be applied to each bale (Continued)

to indicate moisture content for selected portions of the bale since moisture content may differ between flakes in the bale.

14 Claims, 9 Drawing Sheets

(51) Int. Cl.
*A01F 15/04* (2006.01)
*A01F 15/10* (2006.01)

(52) U.S. Cl.
CPC ........ *G01N 33/0098* (2013.01); *A01F 15/042* (2013.01); *A01F 15/101* (2013.01)

(58) Field of Classification Search
CPC ................ A01F 15/101; A01F 15/0816; A01F 15/0825; A01F 2015/076; A01F 2015/0866; A01F 2015/102
USPC ........................................ 100/2, 4, 7, 19 R
See application file for complete search history.

(56) References Cited

U.S. PATENT DOCUMENTS

| | | | |
|---|---|---|---|
| 3,895,571 A | 7/1975 | Freeman | |
| 4,080,563 A | 3/1978 | Marsh et al. | |
| 4,269,116 A | 5/1981 | Gordon et al. | |
| 4,451,781 A | 5/1984 | Anderson | |
| 4,508,737 A | 4/1985 | Forest et al. | |
| 4,567,998 A | 2/1986 | Cole et al. | |
| 4,676,153 A | 6/1987 | Ast | |
| 4,812,741 A | 3/1989 | Stowell | |
| 4,868,491 A | 9/1989 | Black | |
| 6,233,840 B1 | 5/2001 | Finney | |
| 6,278,412 B1 | 8/2001 | Kelly et al. | |
| 6,298,646 B1 | 10/2001 | Schrag et al. | |
| 6,377,058 B1 | 4/2002 | Pemrick | |
| 6,610,341 B2 | 8/2003 | Vinelli | |
| 7,231,814 B2 | 6/2007 | Platon et al. | |
| 7,415,924 B2 | 8/2008 | Roberts | |
| 7,621,111 B2 | 11/2009 | Roberts | |
| 7,743,699 B1 | 6/2010 | Freeman et al. | |
| 7,900,556 B2 | 3/2011 | Freeman et al. | |
| 8,113,110 B2 | 2/2012 | Kraus | |
| 8,539,878 B2 | 9/2013 | Verhaeghe et al. | |
| 8,596,194 B2 | 12/2013 | Kraus | |
| 8,677,896 B2 | 3/2014 | Vanhoutte et al. | |
| 8,860,443 B1 | 10/2014 | Roberts | |
| 9,986,690 B2 * | 6/2018 | Younk | A01F 15/08 |
| 2003/0087116 A1 | 5/2003 | Wood et al. | |
| 2005/0172701 A1 | 8/2005 | Loucks et al. | |
| 2005/0189953 A1 | 9/2005 | Stehr et al. | |
| 2010/0032498 A1 | 2/2010 | Kelly et al. | |
| 2010/0107904 A1 | 5/2010 | Kelly | |
| 2010/0242747 A1 | 9/2010 | Kraus | |
| 2011/0068809 A1 | 3/2011 | Falbo et al. | |
| 2013/0112092 A1 | 5/2013 | Vanhoutte et al. | |
| 2013/0319263 A1 | 12/2013 | Roberts et al. | |
| 2014/0081587 A1 | 3/2014 | Roberts | |
| 2014/0157999 A1 | 6/2014 | Verhaeghe et al. | |
| 2014/0158000 A1 | 6/2014 | Kraus | |
| 2017/0287303 A1 * | 10/2017 | Lang | A01F 15/071 |

FOREIGN PATENT DOCUMENTS

| | | |
|---|---|---|
| CA | 1045447 A | 1/1979 |
| CA | 2455584 A1 | 2/2003 |
| CA | 2638553 A1 | 2/2010 |
| DE | 2614495 A1 | 10/1977 |
| DE | 2614496 A1 | 10/1977 |
| DE | 2849902 A1 | 5/1979 |
| EP | 1364595 A1 | 11/2003 |
| EP | 1535506 A1 | 6/2005 |
| GB | 212032 A | 3/1924 |
| GB | 1504114 A | 3/1978 |
| GB | 1504115 A | 3/1978 |
| GB | 2008380 A | 6/1979 |
| WO | 03011046 A2 | 2/2003 |

OTHER PUBLICATIONS

Screenshots from home page at www.gazeeka.com, retrieved on Feb. 5, 2015, 4 pages.
Canadian Office Action dated Oct. 26, 2018 in CA Application No. 2,924,439, filed on Mar. 22, 2016, pp. 11.
Australian Examination Report dated Apr. 18, 2019 in AU Application No. 2016201815, filed on Mar. 22, 2016, pp. 3.

* cited by examiner

DEVICE AND METHOD FOR TRACKING AND MARKING BALED FORAGE MATERIAL

CROSS REFERENCE TO RELATED APPLICATIONS

This application is a continuation in part of U.S. application Ser. No. 14/667,494 filed on Mar. 24, 2014, now U.S. Pat. No. 9,986,690 and entitled: Device and Method for Tracking and Marking Baled Forage Material with Sensed Moisture Content", this related application being incorporated by reference herein in its entirety.

FIELD OF THE INVENTION

The invention generally relates to tracking of measured parameters for forage material that is baled and stored for subsequent feeding of livestock, More particularly, the invention relates to a device and method in which various measured parameters are used to determine optimal treatment of the forage material upon harvesting, and in which the baled forage material is marked to reflect the status of the bale The measured parameters of the forage material may include moisture content, density, volume, temperature, and nutrition value.

BACKGROUND OF THE INVENTION

Forage materials such as hay crops and corn may be treated upon harvesting in which conditioners are applied to the crops prior to bailing or chopping for storage purposes. The conditioners may commonly be referred to as "inoculants". These inoculants are used to treat the forage material to increase the storage life of the forage material and to prolong the nutritional value of the material.

Excess moisture content for hay crops stored in bales presents many problems. One problem is that the excess moisture in the material promotes the growth of bacteria and fungus that can unduly contaminate the forage material, and can reduce the effective storage life and nutritional value of the forage material.

Another well-known problem is that excess moisture in baled forage material presents a significant risk of fire. The growth of bacteria within baled hay can produce surprising amounts of heat, resulting in spontaneous combustion of over-heated forage material.

In more recent times, commercial baling machines are capable of processing relatively large bales of hay as compared to earlier times in which bales of hay were of significantly smaller size. For example, there are a number of commercially available bailing machines today that are able to produce both square and round bales that may weigh thousands of pounds. Because of the increased size of these bales, there is an increased chance that a fire may occur simply because there is a significantly increased amount of forage material that is tightly packed as compared to the historically smaller bales. Even if the larger bales are strategically spaced from one another in order to allow adequate ventilation between bales, a fire potential may still exist because of the significantly increased bale sizes. Certainly, if large numbers of bales are not capable of being stored in a facility large enough to allow for adequate spacing between bales, the potential for a fire remains of considerable concern.

It is known to selectively apply the inoculants to forage material where certain moisture parameters are measured, and the amount of inoculants applied is adjusted to account for the measured parameters. Moisture content of the harvested crop is but one measured parameter. One noteworthy shortcoming with respect to many prior art systems is that the moisture content of the harvested crop is not measured until that particular portion of the crop has been baled. Accordingly, any adjustments made as to the type or amount of inoculants applied is conducted retrospectively and not based upon the actual portion of the harvested crop that enters the processing machine.

The moisture content of a field containing crops may widely vary within relatively small areas. For example, slight depressions in the field or other factors may result in one spot of the field to retain a significant amount of moisture as compared to other areas that are close in proximity to the particular spot. Because of the wide variances in moisture content, it becomes very difficult to accurately measure the moisture content of a windrow of forage material entering the intake of a baling machine. As a windrow enters the machine, it is laterally dispersed and must be funneled into a smaller area prior to entering a compaction chamber of the baling machine. Because the forage material is initially dispersed but then quickly funneled, it is difficult to measure moisture content since the material undergoes rapid positional changes. Accordingly, the problems with measuring moisture content at the intake of a baling machine is why many prior art systems measure moisture content when the forage material is highly compressed in a bale. The more stable and compressed condition of forage material within the bale is much easier for measuring moisture content. The inherent difficulty in measuring moisture at the intake of a baling/chopping machine, coupled with the retrospective moisture analysis in the prior art devices, results in an inaccurate application of adjusted amounts of applied inoculants.

One solution to the problem regarding inaccuracies associated with measuring of moisture content after the bale has been formed is addressed in the Applicant's prior U.S. Pat. No. 7,743,699. This reference more particularly discloses an automated system and method for measuring moisture in which real time data measurements are taken for relative humidity and moisture content of the forage material in order to timely adjust the amount of an inoculant applied to the forage material thereby more effectively conditioning the forage material. Data gathering capabilities are provided with a system controller to enable an operator to view, adjust, and record various production records, as well as detailed information as to the amounts of inoculant applied. The components associated with the system include an inoculant container having a dispense auger to dispense a controlled amount of inoculant which is then conveyed to the intake opening of the baling machine as the forage material enters the machine. The control system includes various sensors positioned at the intake opening of the baling machine which measures moisture content, and optionally the mass or volume of the incoming forage material. The control system provides a number of user interface options for controlling the dispensing of the inoculant product, as well as capturing data relating to the operation of the baling machine and the use of inoculant products. By measuring moisture content as the forage material enters the machine and then distributing the inoculant directly onto the forage material at that location, this method optimizes the amount of inoculants applied to most effectively condition the forage material.

Another aspect of forage material management is the marking of bales with indications of where high moisture material may be found. By marking the bales in this manner, the bales can be selectively stored in a geometrical configuration that optimizes ventilation of those bales that may have relatively high moisture contents. In this way, the shelf life of the bales may be increased, and fire hazards may be reduced.

One known method of marking bales involves measuring the moisture content of a bale after it has been formed, and then marking the bale with an indication of whether the bale has an out of range moisture condition. The advantage of this method is that both measuring the moisture content of the bale and marking of the bale can be completed at a single station/location in which reliable marking can be achieved at least with respect to marking of individual bales. However, there also a number of drawbacks associated with this method. One disadvantage is that, particularly for larger bales produce from many commercial balers, each bale may have widely varying moisture contents at different locations within the bale. Accordingly, the measurement taken as of the moisture content of the bale greatly depends upon exactly where the moisture is sensed and recorded. For example, in a field in which windrows are small in size, it may take a relatively large area of windrows to produce a single bale of forage material. Accordingly, there can be great variations in moisture content across a single bale and therefore marking of the bale depends on what may be a relatively random moisture sample taken to trigger the marking. Another problem associated with some similar methods is that moisture content measured after the bale has been formed may be used to control the amount of inoculants applied to the forage material as the forage material enters the baling machine. As one can appreciate, the significant distance between the intake area of the baling machine and where moisture is measured after a bale has been formed can result in less than optimal inoculant application since moisture is not measured where the forage material enters the machine.

Therefore, there is a need for precisely and accurately marking bales as to the corresponding moisture content for not only bales observed as a whole, but also for discrete portions of a bale that may have widely varying moisture contents. There is also a need for an integrated moisture content measuring and moisture marking system in which not only is an optimum amount of inoculant applied to forage material, but also precise and accurate moisture measurements are made on the discrete portions of forage material that ultimately become compressed and packed together within a bale. This optimum moisture measurement protocol can therefore enable more precise and accurate marking of bales as to corresponding moisture content within discrete portions of a single bale.

As set forth below in the following description and illustrations of the present invention, each of the aforementioned needs are met with the invention to include others more specifically set forth.

SUMMARY OF THE INVENTION

The invention includes a device and method for tracking and marking bailed forage material with known or sensed moisture content. According to the device of the invention, the moisture content of forage material entering the intake of a processing machine, such as a baling machine, is measured prior to the forage material being transferred to a baling chamber of the machine. Depending upon the sensed moisture content, an inoculant may be applied to the forage material at the intake area of the machine. A series of discrete amounts of forage material enter the baling chamber, and a plunger or compressing element periodically compresses the discrete amounts of forage material as they enter the baling chamber. These discrete sections or portions of forage material are referred to as "flakes". Moisture sensor reading can be taken in rapid succession so that each flake of material may have a recorded moisture content reading. A number of flakes make up a single bale of material. For larger bales formed in many of the newer commercial baling machines, there can be as many as 60 flakes formed within a single bale. Accordingly, there can be just as many moisture measurements in which detailed moisture content is therefore recorded for each separate portion or flake of a selected bale.

As the forage material passes through the baling machine, the discrete portions of the forage material are linearly tracked so that these discrete portions of the forage material may be appropriately marked with an indication of moisture content or other attributes observed. With respect to moisture content, the invention provides for a number of options for marking a bale as it exits the baling chamber of the machine into the bale chute of the machine. For example, high moisture content flakes can be marked with a spray at the corresponding locations where high moisture content forage material may be found within a particular bale of material. Another marking option is to provide a marking on the bale which not only indicates a high moisture condition, but also providing a marking with the generally corresponding area of the bale which may have the highest or lowest moisture condition. Accordingly, a spray applied to the bale may have a particular pattern applied to the bale indicative of corresponding portions within the bale having sensed out of range moisture conditions. For example, a series of dots, or a continuous spray over a selected length of the bale may indicate exactly where out of range moisture conditions may exist within the bale.

Another potential marking option is to mark a bale with an indication of where inoculant material has been applied to the bale in response to sensed out of range moisture conditions. For example, a bale could contain two distinct sets of markings, one marking indicating locations in the bale where high moisture conditions may exist, and another set of markings which may indicate the locations where the forage material within the bale has received an application of inoculants. By comparison of these marked parameters, a user may identify/confirm the status of a particular bale to determine whether or not it may have been adequately conditioned considering the sensed moisture content. As mentioned above, because some bales may have widely varying moisture contents within a single bale, the invention specifically contemplates a precise and accurate marking capability in which discrete sections of forage material are tracked as they pass through the baling machine such that corresponding precise and accurate markings may be applied to the bale indicating the observed/sensed parameters.

With respect to providing the capability to track the locations of discrete portions of forage material, a plurality of sensors or sensor stations are provided within the baling machine to accurately track the forage material as it passes through the machine. A first group of sensors may be provided at the intake of the baling machine to determine the presence or absence of forage material entering the machine at that particular time. In this regard, optical sensors may be mounted on the lateral side rails or lateral supports of the intake portion of the baling machine such that the presence or the absence of forage material can be determined, along with the corresponding times in which the presence or absence is observed for recording within a time sequence. More than one optical sensor can be used to determine relative amounts of forage material that may enter the intake area so that the approximate volume of forage material entering machine at a particular time can later be used to determine amounts of the forage material making up a flake within a known period of time.

Another sensor or sensor station of the invention is one that is used to positionally track the location of the forage material as it passes through the baling machine. More specifically, this sensor station is used to track the linear movement or progression of the forage material by observing the rotational position of a star wheel which is commonly used on the bale chute of a baling machine to determine when a length of compressed forage material should be separated into respective bales. The star wheel, in most applications, serves as a sort of mechanical timer. The tines or protrusions of the star wheel art inserted within the forage material, and the star wheel rotates in response to the linear movement of the compressed forage material as it passes from the baling chamber through the bale chute. Rotation of the star wheel indicates an incremental amount of passing forage material which ultimately triggers the operation of a needle assembly to separate and tie a predetermined length of compressed forage material into a bale. The sensors of the invention located at the star wheel observe and record the rotational movement of the tines, and therefore are capable of recording precise relative movement of discrete portions of the forage material as they pass through the machine.

According to one preferred embodiment of the invention, the sensor station located adjacent the star wheel may be provided in pairs of sensors so that both forward and reverse movement of the compressed forage material may be observed. A plunger of the baling machine compresses new forage material introduced into the baling chamber. The plunger is cyclically retracted in order that new forage material may enter the baling chamber. When the plunger is retracted, there may be some recoil of the forage material that may result in a relatively small backward or rearward movement of the forage material until the next flake of forage material is introduced and compressed. Ultimately, the forward movement of the forage material through the machine is greater than the recoil which allows the forage material to advance completely through the machine. The sensors can be positioned to "count" the rotation of the tines of the star wheel, and therefore differentiate between rotation of the star wheel corresponding to forward and rearward movements of the forage material.

Another sensor or sensor station associated with the invention is one which is located adjacent the needle assembly of the baling machine, and which is able to sense the rotational movement of the needle assembly in separating respective bales. Accordingly, this observed information along with the linear tracking feature of the invention enables precise and accurate spray patterns to be applied to the respective bales as discussed in more detail below.

In terms of applying a marking to the bales, in one preferred embodiment of the invention, a plurality of spray applicators such as spray paint cans may be used for application of selected patterns and colors of paint to be applied. The spray nozzles of the spray applicators may be electrically controlled to apply appropriate markings. For example, a solenoid switch may be used to activate or deactivate the spray nozzles of the spray applicators in order to selectively apply the markings. In this regard, the invention also further includes an onboard controller which is capable of executing commands for control of the solenoid switches to thereby activate the spray applicators.

Inputs to the controller include each of the sensors used to determine the location of discrete portions of the forage material. Additional inputs to the controller include the measured moisture contents of the discrete portions of the forage material and whether inoculant has been applied to those discrete portions. For purposes of determining amounts of inoculants to be applied, another input to the controller may include relative humidity conditions. In connection with operator control of the device, the controller may further include the ability to display user interfaces for the user to determine how markings should be applied to the bales, as well as the manner in which inoculants should be applied to the forage material having measured moisture content. According to one aspect of operator control, an operator may have the ability to determine a threshold moisture content in order to trigger marking of a selected bale, as well as to determine whether the selected bale should be marked with an indication of whether an inoculant was applied to the bale. According to another aspect of operator control, the operator may also have the ability to select different spray patterns as well as different colors of spray in order to indicate the particular condition of the selected bale. For example, one color may indicate sensed locations of high moisture content, and another color may indicate a corresponding application of inoculant applied to the bale, which may correspond to those locations where high moisture content was sensed.

In yet another aspect of operator control, it is also contemplated that in lieu of different colors applied to the bale, other differentiating types of markings can be applied to indicate the status of the selected bale. For example, the upper portion of the bale as it proceeds through the bale chute may be the dedicated portion of the bale reserved for marking moisture content, while the presence of an applied inoculant may be applied to the lower portion of the bale dedicated for markings related to applied inoculants. Accordingly, it is contemplated that the spray applicators can be oriented at different heights at the bale chute so different portions of the bales can be marked with the appropriate markings corresponding to locations on the bale intended to receive such predetermined markings. Because of the relatively large surface areas of the sides of bales, multiple markings can be applied to the bales at different height locations on the bales.

Taking into consideration the many options provided for marking a bale, it is further contemplated that a plurality of spray applicators may be individually controlled by the controller, in which each spray applicator applies a marking corresponding to a particular predetermined marking protocol. It is also contemplated that redundant spray applicators cans be provided so that in the event one spray applicator is empty, another spray applicator will be activated thus eliminating the need to stop the baling machine in order to replace the empty applicator.

In addition to measurement of moisture content and relative humidity, there are a number of other parameters that can be measured and used as inputs to the controller in order to further optimize application of inoculants and marking of the bales. These other parameters may include forage material density, volume, and temperature. Another observation that can be taken is to determine the nutrition value of the forage material, and to the extent the observations are quantified, this observation can also be characterized as a measured parameter.

For measurement of the volume of the forage material, this measurement will account for variances in volumes which can allow for further adjusting the rate of inoculants applied. For example, forage material with a relatively high volume will presumably require lesser amounts of inoculants because of the air spaces or gaps between the strands or straws of material. Forage material with relatively lower volumes will presumably require greater amounts of inoculants because there is a greater mass or amount of forage material within the same volume. There are many environmental factors that may affect the particular volume of the forage material at any point in time; therefore, having the ability to measure volumes of material allows for yet a greater certainty in the application of desired quantities of inoculants. For volume measurement, one preferred method of measuring this parameter is by an ultrasonic sensor that may be positioned at the intake area or in front of the intake area just prior to the forage material entering the baling machine.

Another measured parameter that can be used as an input to the controller in order to further optimize application of inoculants includes the temperature of the forage material as it is picked up. The temperature of the forage material at the time the material is baled will affect the subsequent heat and moisture that builds within the bale over time. In general, forage material with a greater temperature will contribute to greater heat and moisture within the bale over time, while forage material with a lesser temperature will contribute a lesser amount to the heat and moisture within the bale. Particularly for forage material that may be baled during high temperatures, providing a temperature input to the controller will allow for an adjusted amount of inoculants to be applied. For temperature, one preferred method of measuring the temperature is by a thermal imaging sensor (thermography) that may be positioned at the intake area or in front of the intake area just prior to the forage material entering the baling machine Yet another measured parameter that can be used as an input to the controller in order to further optimize application of inoculants includes the density of the forage material as it is picked up. The volume and density of the forage material are related; however, different types of sensors can be used to measure these parameters. For density, one preferred method of measuring the density is by a microwave sensor that is positioned at the intake area or in front of the intake area just prior to the forage material entering the baling machine.

Yet another measurement that can be taken, which may not necessarily be an input to the controller, but may otherwise be valuable to an owner of the forage material is to conduct measurements of nutritional analysis. One method of conducting this type of analysis is to take images of the forage material as it is picked up into the baling machine to determine nutritional analysis. One preferred method of conducting the nutritional analysis is by imaging of the forage material by near infrared (NIR) sensors that generate images in this wavelength. This method may be generally referred to as near infrared spectroscopy in which the nutritional content of the forage material can be analyzed and then marked on the bale of forage material instantly. Providing an estimate of the monetary value of the bale of forage material based upon the nutritional analysis provides a commercial advantage since the monetary value can be used to initially sort and distribute the baled forage material as opposed to sorting and distributing later.

Considering the above features and advantages of the invention, in one aspect, the invention may be considered a device for tracking and marking baled forage material comprising: a first sensor station for determining incremental linear movement of the forage material within a baling chamber of the machine and movement of the forage material as it passes from the baling chamber through a bale chute of the machine; a plurality of sensors located near an intake area of the baling machine that receives the forage material, said sensors including at least one of a moisture sensor, an ultrasonic sensor for volume measurement of the forage material, a thermal imaging sensor for temperature measurement of the forage material, a microwave density sensor for density measurement of the forage material, and an NIR sensor for nutrition analysis to determine selected nutritional components of the forage material; a controller for receiving input signals from the sensor stations and the plurality of sensors to determine (1) the incremental linear advancement of discrete portions of the forage material as they pass through the baling machine and (2) to determine measured parameters from the input signals from the plurality of sensors, and wherein said controller transmitting control signals for purposes of marking bales with an indication of the measured parameters of the forage material including at least of one of moisture content, temperature, density and nutritional components; and a marking station for marking the bales as they have passed through the baling machine, said marking station creating marks on the bales in response to control signals transmitted from the controller indicative of at least one of the measured parameters.

According to other more particular aspects of the invention related to this first aspect of the invention, the invention may include various sub-combinations of these recited features, or may include other features.

According to another aspect of the invention, it may be considered a system for tracking and marking baled forage material comprising: a linear movement sensor station for determining linear movement of the forage material within a baling chamber of the machine and movement of the forage material as it passes from the baling chamber through a bale chute of the machine; a plurality of sensors located near an intake area of the baling machine that receives the forage material, said sensors including at least one of a moisture sensor, an ultrasonic sensor for volume measurement of the forage material, a thermal imaging sensor for temperature measurement of the forage material, a microwave density sensor for density measurement of the forage material, and an NIR sensor for nutrition analysis to determine selected nutritional components of the forage material; a controller for receiving input signals from the sensor stations and the plurality of sensors to determine (1) the incremental linear advancement of discrete portions of the forage material as they pass through the baling machine and (2) to determine measured parameters from the input signals from the plurality of sensors, and wherein said controller transmitting control signals for purposes of marking bales with an indication of the measured parameters of the forage material including at least of one of moisture content, temperature, density and nutritional components; and a marking station for marking the bales as they have passed through the baling machine, said marking station creating marks on the bales in response to control signals transmitted from the controller indicative of at least moisture one of the measured parameters.

According to other more particular aspects of the invention related to this second aspect of the invention, the invention may include various sub-combinations of these recited features, or may include other features.

According to yet another aspect of the invention, it may be considered a method for tracking and marking baled forage material, comprising: (i) determining linear movement of the forage material within a baling chamber of the machine and movement of the forage material as it passes from the baling chamber through a bale chute of the machine by a linear movement sensor station; (ii) determining and tracking respective locations of portions of the forage material by a controller as the forage material passes through the baling machine, wherein each portion has at least one corresponding measured parameter as measured by a corresponding parameter sensor communicating with the controller; (iii) receiving input signals by the controller from the sensor station reflective of relative positional changes of the forage material passing through the baling machine; (iv) receiving further input signals by the controller from the parameter sensor; (v) transmitting bale marking commands from said controller to a marking station for marking the bales, said bale marking commands being transmitted for purposes of marking bales with an indication of at least one measured parameter of the forage material including at least one of moisture content, volume, temperature, density, and nutrition content; and (vi) marking the bales by the marking station in which marks are created in response to the bale marking commands transmitted from the controller indicative of at least one measured parameter for corresponding portions of the bales According to other more particular aspects of the invention related to this third aspect of the invention, the invention may include various sub-combinations of these recited features, or may include other features.

Ultimately, the invention provides a number of options for precisely and accurately marking bales as to a number of measured parameters and applied inoculants. Other features and advantages of the invention will become apparent from a review of the following detailed description, taken in conjunction with the drawings.

DETAILED DESCRIPTION OF THE INVENTION

Figure 1:
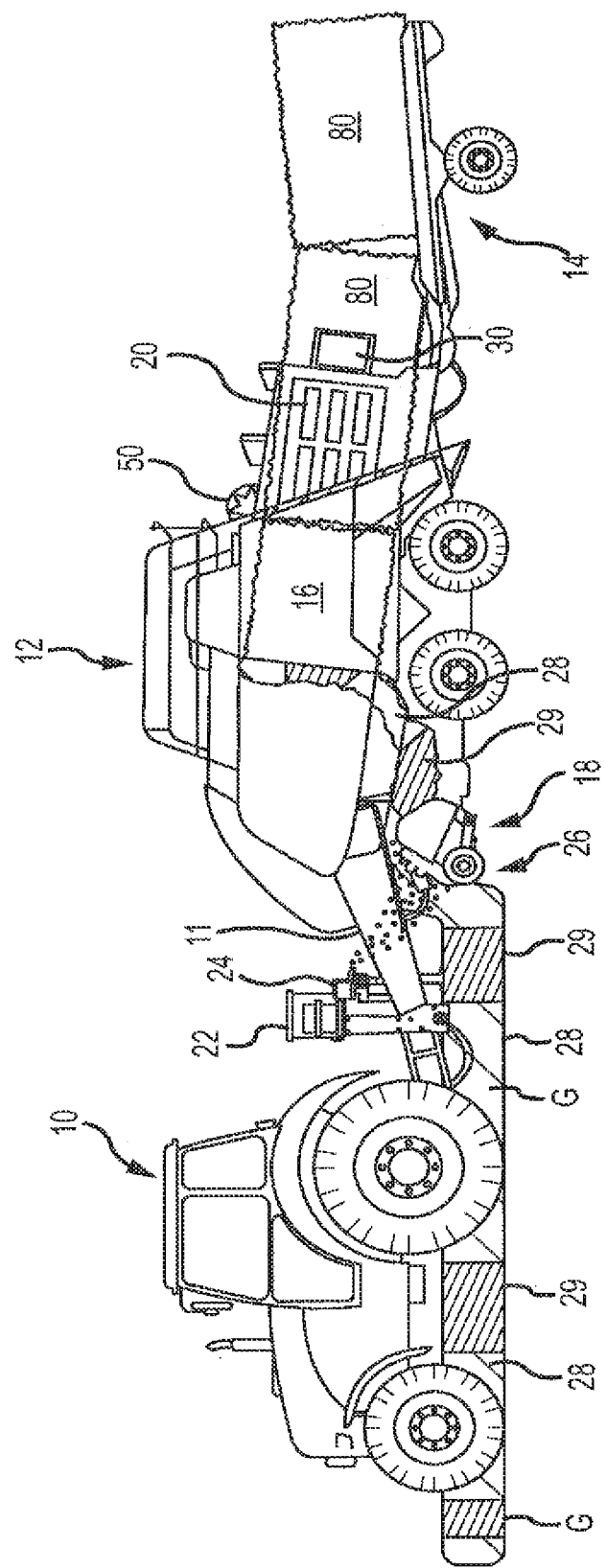
FIG. 1 illustrates a prior art baling machine and components therein used to make bales in which bales are evaluated/sensed for moisture content, inoculants are applied to the forage material in response to high moisture readings, and bale markings are applied according to the observed moisture content readings.

FIG. 1 illustrates a prior art system for making bales of forage material. Specifically, FIG. 1 illustrates a tractor 10 towing a large square baler 12. The baler 12 generally includes a frame which carries a baling chamber 16 with associated components which are used to enclose and subsequently compress gathered forage material into a bale. An intake area 18 of the baler includes a pickup rotor or reel 26 which picks up and advances forage of material from the ground G into the machine. A bale chute 20 is positioned at the trailing end of the machine, and directs formed bales away from the machine. A bale accumulator 14 may be used to temporarily receive and hold a number of formed bales 80 for subsequent transfer to a storage location.

FIG. 1 further illustrates forage material 28 and 29 that can be distinguished by differences in moisture content, and this figure is intended to illustrate that forage material may have varying moisture contents in separate and discrete areas of a particular windrow which is worked by the baling machine. FIG. 1 also shows an inoculant storage tank 22 mounted to the towing tongue of the baling machine 12, along with an inoculant applicator or dispenser 24 which dispenses inoculants onto the forage material within the intake 18 of the machine. In connection with applying inoculants at this location, reference is made to the Applicant's prior U.S. Pat. No. 7,743,699 which is incorporated by reference herein in its entirety for purposes of disclosing how inoculants are applied in response to moisture content that is measured at the intake area 18 of the machine 12, and as also discussed with respect to FIG. 4 herein.

FIG. 1 also illustrates a prior art moisture sensing and marking system 30. This system 30 measures moisture of the bale as it passes through and beyond the bale chute 20. Once the moisture reading has been taken, the bale is marked with appropriate markings to indicate moisture content. One type of sensor used in prior art systems 30 is a microwave sensor which is capable of penetrating the bale in order to take moisture measurements within the interior of the bale. A star wheel 50 is shown as being mounted to the upper portion of the bale chute, and as mentioned, the star wheel is used as a mechanical position sensing element to determine the advancing positions of forage material as it exits the baling chamber, so that bales may be subsequently separated and tied.

Figure 2:
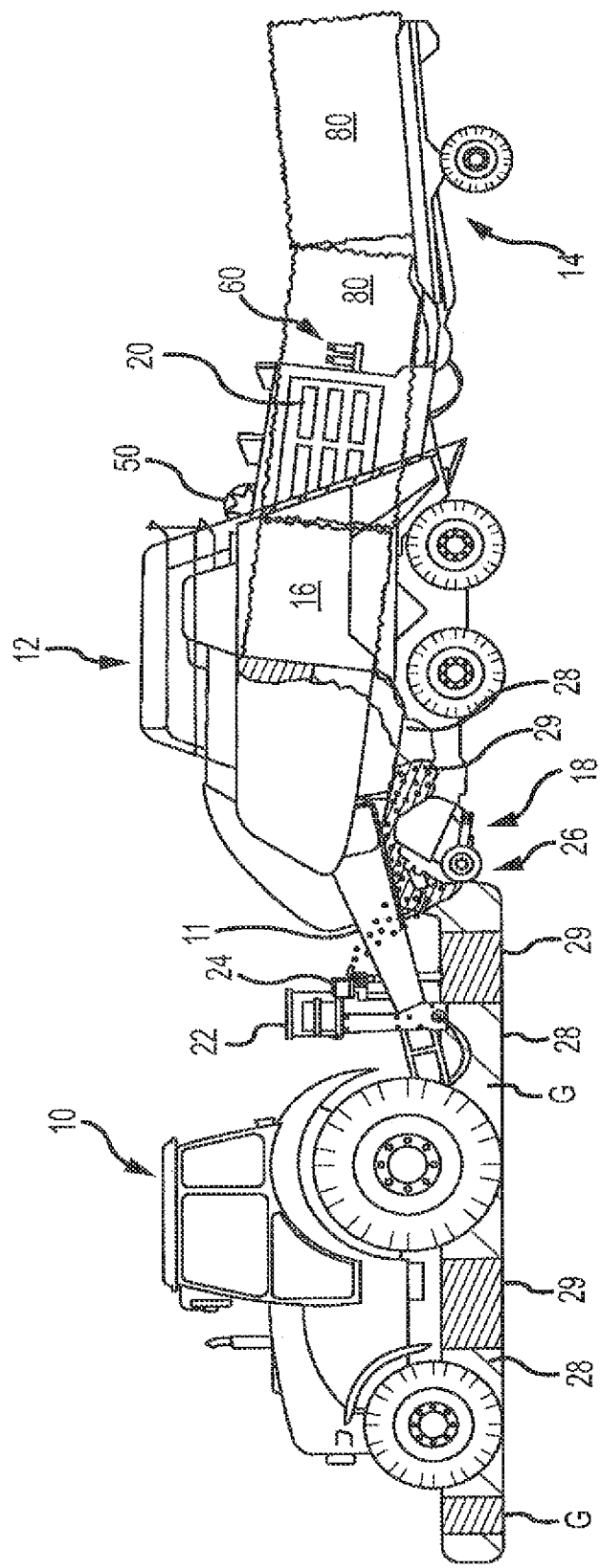
FIG. 2 illustrates certain features of the device and method of the present invention for tracking and marking bailed forage material with sensed moisture content.

FIG. 2 illustrates the device and method of the present invention. The same reference numerals in this figure correspond to the same elements from FIG. 1. From the view of FIG. 2, the only illustrated difference between it and FIG. 1 is the elimination of the moisture sensing and marking system 30 in favor of a marking station 60 located at the trailing end of the bale chute 20. However, other differences of the invention are explained below.

Figure 3:
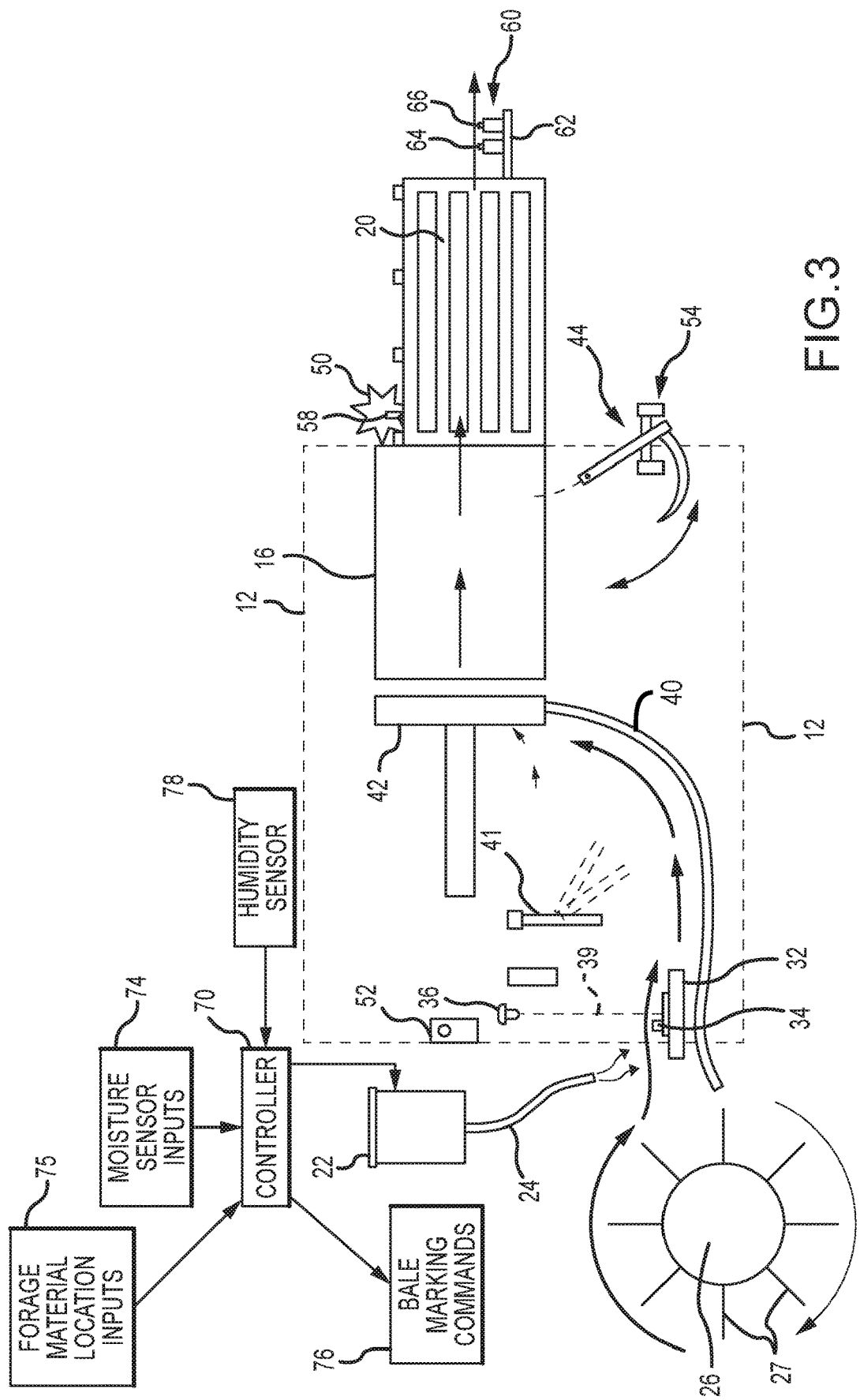
FIG. 3 is a schematic diagram illustrating features and components of the invention.

Referring to FIG. 3, a schematic diagram is provided to explain the elements and functioning of the device and method of the present invention. The intake area 18 includes the pickup reel 26 and a plurality of projecting teeth or tines 27 that convey the forage material into the baling machine 12 through a gap or space which communicates downstream with a chute feeder or conveyor 40. In the gap or space at the opening into the machine, various types of sensors may be mounted for measuring the moisture content of the forage material. A feed assist device 41 may be incorporated to help convey the forage material along the chute feeder 40 into the baling chamber 16 of the machine 12. This device 41 may include a plurality of fingers or projections that rotate or otherwise move in a manner to advance the forage material along the chute feeder 40. A plunger 42 moves in a reciprocating fashion to compact the forage material in the baling chamber 16 and to receive incoming forage material from the chute feeder 40.

An inoculant container 22 holds a quantity of inoculants to be dispensed by a dispensing element 24, which may include a dispense auger, a pressurized dispense line, among others. According to the invention, the inoculants are preferably applied to the forage material prior to it being conveyed to the baling chamber. The amount of inoculants applied is determined by a controller 70. Moisture content of the forage material is measured by one or more sensors 34 and/or 36. The location(s) at which measurements are taken can be referred to as measurement points. Moisture sensor readings are provided as inputs 74 to the controller. A humidity sensor 78 may also supply inputs to the controller. The controller 70 adjusts amounts of inoculants applied by speeding up or slowing down a motor that may drive the dispense auger, or a pump that may convey liquid inoculants through a dispensing line and nozzle. The controller is therefore responsive to the inputs to provide an adjusted dispensing rate for inoculants within a very short time span in order that inoculants applied correspond to the section or portion of forage materials which have been sensed as being at a particular moisture content warranting application of inoculants to that portion/section. Inoculants are intended to be applied in varied amounts to account for discrete portions of forage material that may have significant moisture content differences over relatively short windrow distances.

Sensor 34 is intended to represent a contact type moisture sensor mounted to the packer pan 32. Alternatively, the sensor 34 may be mounted to a support with load cells (not shown) for measuring the weight of incoming forage material, in which weight is also another parameter that could be measured and recorded by the controller. Contact type sensors may include conductive strips that provide a variable voltage signal back to the controller based upon measured conductivity, which directly correlates to moisture within the forage material. Other examples of contact sensors may include probes that extend into the path of the forage material as it passes over the packer pan, and contact of the probes against the forage material may result in measurement of moisture content.

According to another method of measuring moisture content, the sensors 34 may represent resistance measuring sensors that provide a resistance based electrical signal to the controller. The resistance based electrical signal from the sensor is conditioned by the controller to change the signal to a corresponding optical wavelength, and the optical wavelength is then read and converted to an electrical resistance output. This processing of the original signal from the sensor is conducted to provide better accuracy readings from the sensor in which intermittent electrical shorts may be eliminated from the readings.

Sensor 36 is intended to represent a non-contact type sensor, such as ultrasound sensors or infrared sensors. Ultrasound sensors may measure relative distances, and the volume of forage material entering the machine can be calculated as a function of the clear distance measured by the ultrasound sensor in the gap or space where the forage material enters the machine. One example of an infrared sensor is one that measures the characteristic absorption of infrared radiation at various wavelengths to determine moisture content within the forage material. For the noncontact type sensor as shown in FIG. 3, a sensing beam has a direct line of sight 39 with respect to the incoming forage material that passes below.

FIG. 3 also illustrates forage material location inputs 75 which are intended to represent all of the electronic signals sent from the sensing stations to the controller as to the locations of forage material as it passes through the baling machine. The groups of sensors may be conceptually separated into three groups or stations of sensors: a first sensor group for sensing the presence or absence of forage material as it enters the machine at the intake area, a second sensor group for determining the incremental movement of forage material as determined by the sensors monitoring the rotation of the star wheel, and a third sensor group for determining the periodic rotational movement of the needle assembly which determines a separation between adjacent bales, all of which affect the location of individual flakes of material as they pass through the machine.

A needle assembly 44 is schematically represented in FIG. 3, the needle assembly including a plurality of needles 46 which are rotated from a stowed or lowered position as shown in FIG. 3, to an upward rotated position through the baling chamber and into compressed forage material therein. The needle assembly is used to position tie string for tying of the bale, and to also separate bales from one another as they progress through the baling chamber 16 into the bale chute 20. As discussed in more detail as set forth in the discussion of FIG. 7, a needle assembly sensor 54 is provided to sense the position of the needle assembly 44 as it rotates each time adjacent bales are to be separated from one another. Accordingly, the sensor 54 serves as an additional linear tracking or linear positioning sensor to convey to the controller the termination of one bale and the beginning of another bale which in turn, affects how the bales are marked at a marking station 60.

As also shown in FIG. 3, the marking station 60 may include a plurality of applicators such as spray paint containers 64 and 66 that are selectively and controllably activated to apply markings to the respective bales as they pass the station 60. The applicators may be mounted on a base 62, and the plurality of spray containers 64 and 66 can be employed within the same marking station. The containers maybe adopted for redundancy in which an extra container is available to extend the effective operation time of the applicator station 60. Alternatively, the different containers 64 and 66 may represent use of different colors to indicate different measured parameters of a bale passing the marking station 60. It is also contemplated in a preferred embodiment that there is a marking station 60 can be located on both sides of the baling machine so that both opposite sides of each bale can be marked. Marking of the bales can be executed so that both sides of each bale are marked with the same information, or an operator could choose to mark each side of the bale with selected different information from a menu of options on a user interface having multiple marking options.

FIG. 3 also shows the star wheel 50 mounted to the upper portion of the bale chute 20. The star wheel penetrates the forage material as it passes through the bale chute 20. Accordingly, the star wheel 50 will rotate in response to the linear movement of the forage material as it exits the baling chamber 16 and passes through the bale chute 20. In prior art baling machines, the star wheel is used as a mechanical position indicator which indicates progressive movement of the forage material so that the needle assembly may then be activated to separate adjacent bales and position tie string. The present invention adds another group of sensors, namely, a plurality of star wheel or linear movement tracking sensors 58 which record the rotational movement of the star wheel, and provide inputs to the controller corresponding to very precise linear movements of the forage material as it passes through the bale chute 20. As set forth in more detail below with respect to the description of FIG. 6, pairs of sensors can be used to observe the movement of the star wheel to account for both advancing or progressive movement of the forage material, as well as rearward or recoil movement of the forage material as may be experienced each time the plunger is retracted within the baling chamber to receive additional forage material conveyed from the chute feeder.

Figure 4:
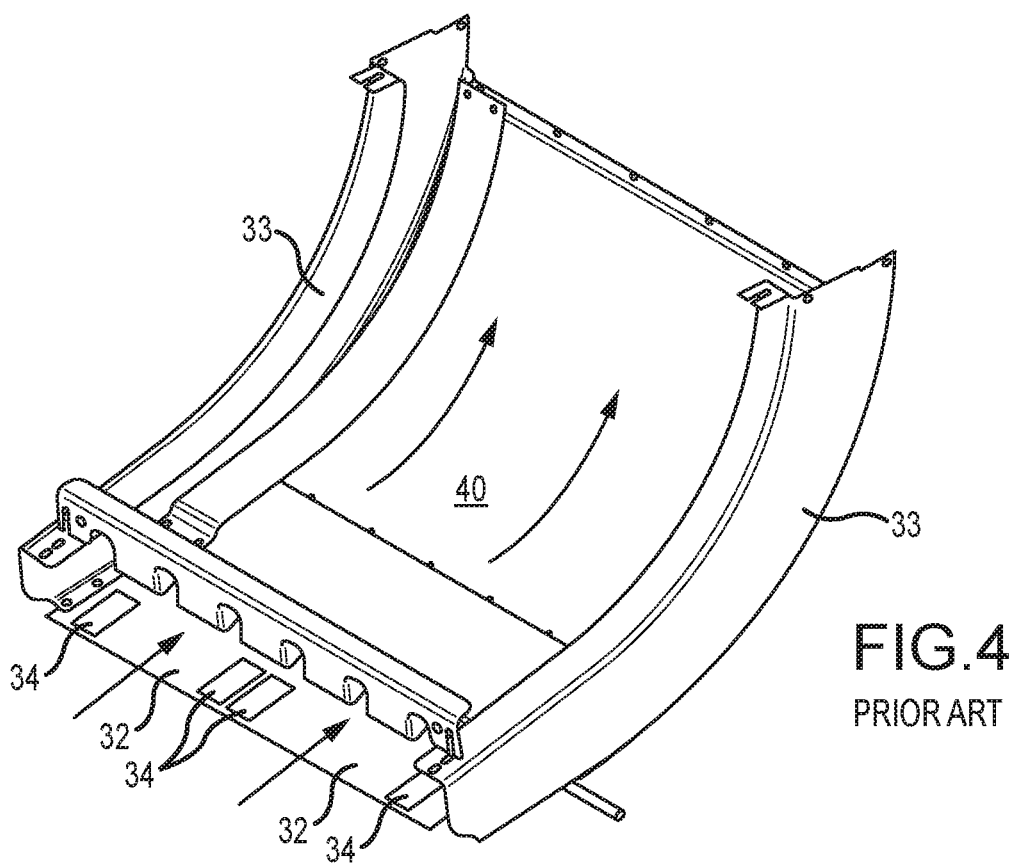
FIG. 4 generally illustrates one prior art example of an intake area for a baling machine to include contact type moisture sensors located on the "packer" pan or plate of the intake area in order to sense moisture content of forage material passing over the pan.

Referring to FIG. 4, this figure provides a more detailed view of the packer pan 32 and the positioning of the contact type sensors 34 that have been adopted in the Applicant's prior invention. As shown, the chute feeder 40 communicates with the packer pan 32 to convey the forage material upwards and into the baling chamber. The forage material is confined between opposing side rails or walls 33 which confines the forage material in its upward travel. The feed assist device 41 (shown in FIG. 3) may assist in conveying the forage material along the chute feeder 40 into the baling chamber 16. The particular sensor arrangement in FIG. 4 illustrates four sensors 34 in which the area of the packer pan is separated into two sensing zones: one sensing zone being defined from one lateral edge of the packer pan to the center, and the other sensing zone being defined from the center to the opposite lateral edge of the packer pan. Separating the forage material into two separate moisture sensing zones may assist with a more accurate determination of actual moisture content as moisture content may also vary laterally across the packer pan. Alternatively, having two moisture sensing zones may assist with timely recording and validation of sensed moisture which may then facilitate a more rapid output to the inoculant applicator.

Figure 5:
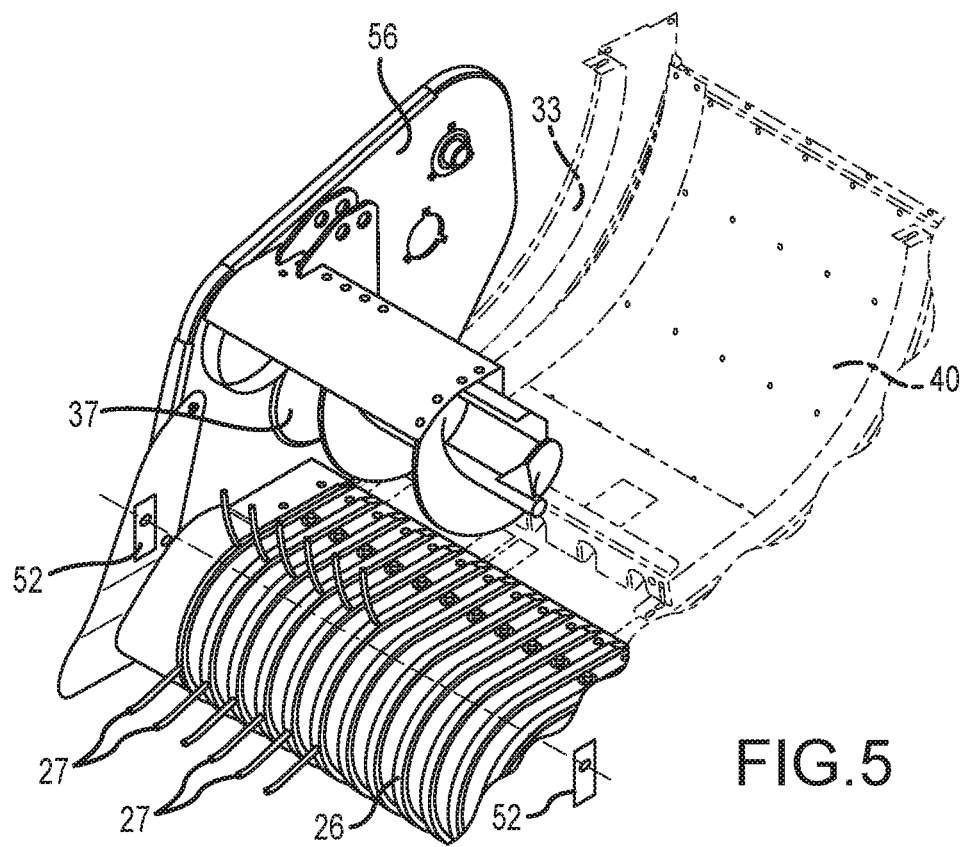
FIG. 5 generally illustrates another example of the intake area for a baling machine, to further include a pickup rotor or wheel which is used to mechanically transfer the forage material from windrows on the ground across the packer pan and through a chute feeder or conveyor located within the interior of the baling machine; this figure further illustrates the location of intake sensors used to determine the presence or absence of forage material entering the baling machine.

Referring to FIG. 5, the subject matter of FIG. 4 is supplemented with further elements of the baling machine to include the pickup rotor/reel 26, and a helical cutter or chopper 37 which cuts the forage material into uniform lengths, and also assists in conveying of the forage material onto the chute feeder 40. As shown, the cutter 37 extends substantially parallel with the rotor 26, and one end of the cutter 37 may be secured adjacent a side panel 56 which also serves to confine the forage material as it enters the machine. In accordance with the present invention, an optical intake sensor 52 may be mounted on the side panel 56 and directly adjacent to the pickup reel 26. In this position, the optical sensor may determine the presence or absence of forage material as it enters the machine. The presence or absence of forage material effects inputs to the controller and the controller is able to calculate and respond to the present situation in terms of tracking amounts of forage material making up flakes when a sufficient amount of material is conveyed to the baling chamber.

Figure 6:
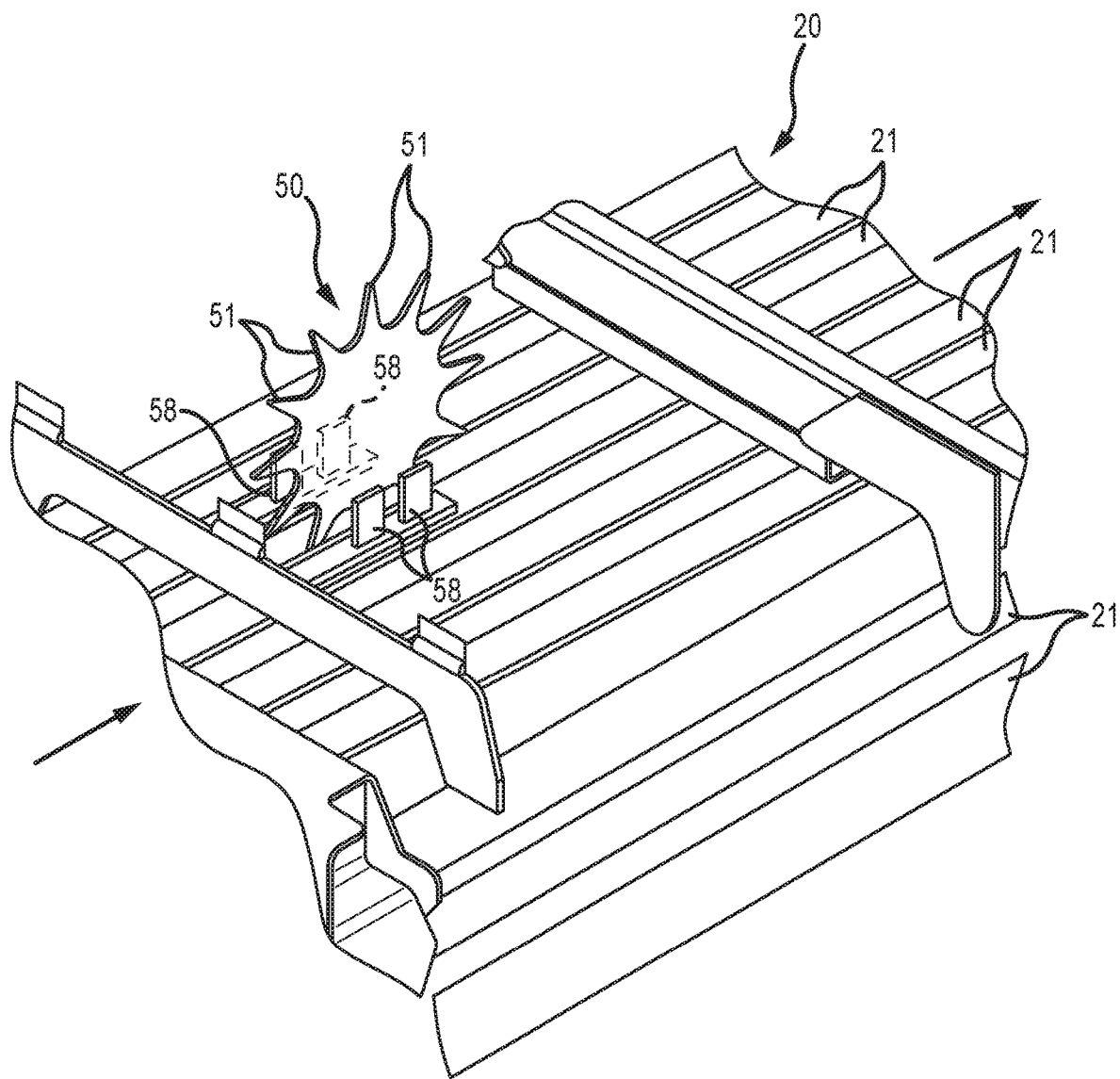
FIG. 6 illustrates the bale chute of a baling machine and a star wheel used as a mechanical position sensing apparatus, along with pairs of linear position tracking sensors of the present invention which record the rotational status of the star wheel.

Referring to FIG. 6, an enlarged portion of the bale chute 20 is illustrated showing the star wheel 50 in its position as it is used to convey relative movement of forage material as it progresses through the baling chamber into the bale chute. More specifically, the star wheel 50 has a plurality of points or tines 51. The tines 51 project through the slats or rails 21 of the bale chute 20 such that the star wheel will rotate in response to movement of the forage material. The star will rotate clockwise according to the view of FIG. 6 in the advanced or forward direction as the forage material exits the baling chamber. As mentioned however, the star wheel 50 may also rotate counterclockwise in a rearward direction in response to some incremental amount of recoil within the bale as result of the plunger being retracted which enables the forage material to temporarily expand. In order to precisely measure the actual amount of forward movement of the forage material, one or more pairs of optical or proximity sensors 58 may be used to record the movement of the tines. In order to confirm forward movement of the forage material, each of the sensors must sense progressive movement, which could be indicated, for example, by first simultaneously one sensor observing a tine and the other sensor observing the gap between the tines, and next, the other sensor observing a gap in the other sensor observing a tine thereby indicating rotation of the star wheel in the forward or advancing direction. Reverse movement of the star wheel may be detected by an opposite pair of sensing in which the star wheel is therefore detected as rotating in or retracted direction. Depending upon the type of sensor chosen (either proximity or optical) and how pairs of sensors are oriented with respect to the tines and gaps between the tines, the signals sent by the sensors to the controller can be interpreted to determine net forward movement. FIG. 6 more specifically illustrates a pair of optical sensors in which changes in sensed light conditions are used to "count" the tine rotations. For example, the sensors can be positioned such that rotation of the tines interrupts an optical path between elements of each sensor. If proximity sensors are used, a single pair of sensors located on the same side of the tines can be used to sense the incremental and changing presence or absence of tines and gaps between tines as the star wheel rotates.

The controller receives and records the inputs from the various sensors, and necessary calculations are made within an algorithm(s) of the controller to confirm the exact location of each flake as it passes through the baling machine. The location data is then used to generate outputs to the marking station 60 so that precise and accurate markings may be applied to the bales 80.

Figure 7:
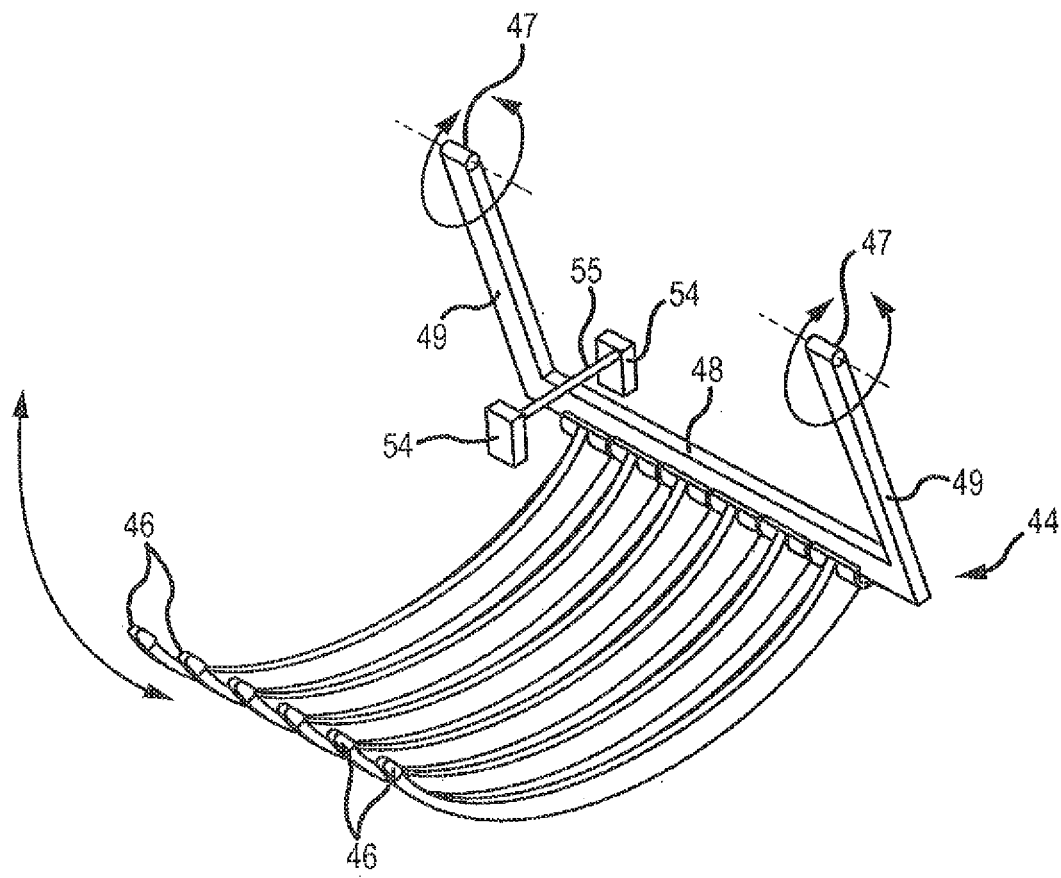
FIG. 7 is a schematic representation of a needle assembly used in the baling machine to separate flakes of forage material and to place tie string material for tying bales as they exit the baling chamber; this figure further showing an example optical sensor for sensing movement of the needle assembly.
Figure 7A:
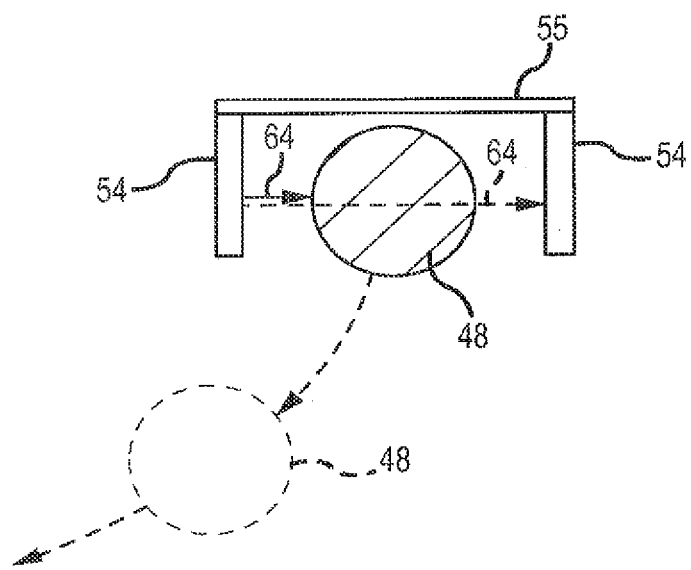
FIG. 7A a is an enlarged schematic representation of how the optical sensor senses movement of the needle assembly.

Referring to FIG. 7, a schematic diagram of the needle assembly 44 is illustrated along with a more detailed view of the needle assembly sensor 54 which is used to observe the cyclical rotation of the needle assembly each time there is a demarcation to be made between adjacent bales. The tips of the needles 46 carry tie material such as twine (not shown) that is used to tie each bale. The needle assembly 44 may generally include a support bar 48, and two support bar extensions 49 which rotate about their respective ends 47. The needle assembly remains in a lowered or stored position as shown in FIG. 7 and is moved to an upper rotated position in order to insert the needles 46 through the forage material. FIG. 7A more specifically illustrates one example of how the needle assembly sensor 54 may be positioned to sense of movement of the needle assembly. As shown, each optical sensing element may be spaced from one another a fixed distance as determined by a sensor spacing element 55. When the needle assembly 44 is in its stowed position, the support bar 48 blocks the optical path 64 between the sensing elements. When the support bar 48 is rotated as shown in the dotted lines, the bar 48 moves away from between the sensing elements, enabling a light path 64 to be travel unbroken between the sensing elements, and thereby enabling the sensing assembly to convey a signal to the controller indicating a change of position. As the needle assembly continues to rotate, the needles continue in an arced path upwards into the baling chamber.

Figure 8:
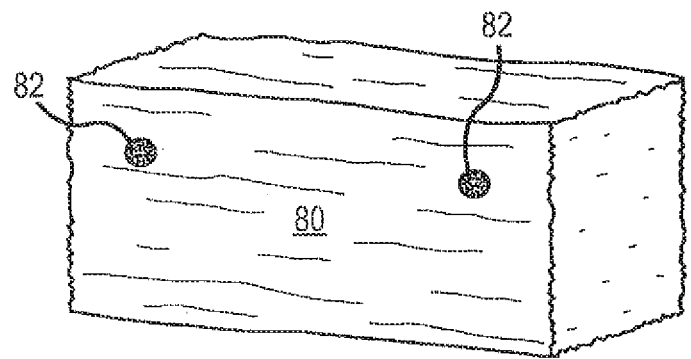
FIG. 8 provides one example of how a bale may be marked according to the present invention.

Referring to FIG. 8, this shows one example of how a particular bale 80 may be marked. Specifically, the bale 80 is marked with two spot indications 82, which may correspond to two locations within the bale that may have out of range moisture content conditions as moisture was measured previously. According to this marking scheme, a single bale is provided with not only one, but two separate and distinct indications of out of range moisture conditions. Further, these two spot indications may indicate differences between the respective measured contents of the two locations. Accordingly, the spots could be made with visual distinctions as by color, size, or location on the bale according a predetermined marking protocol or convention.

Figure 9:
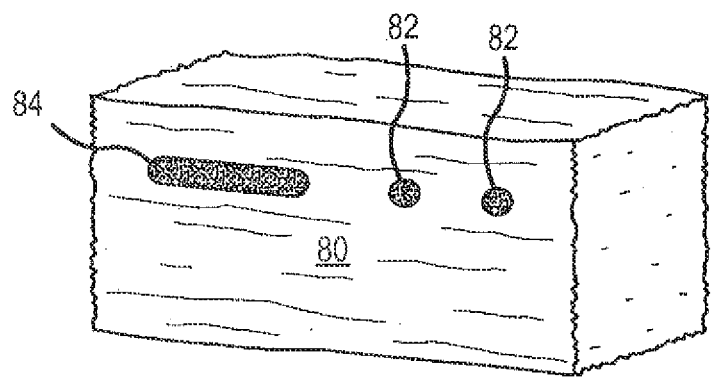
FIG. 9 provides another example of how a bale may be marked according to the invention.

Referring to FIG. 9, this shows another example of how a particular bale 80 may be marked according to another scenario. In this example, the bale includes a spot indication marker 82 indicating where within the bale there is an out of range moisture condition, but also a continuous or extended indication marker 84 that may correspond to a particularly large section of forage material having an out of range moisture condition. For example, the baling machine may have passed a low, wet area on the ground in which the forage material was considerably wetter than forage material on either side of the wet area. Therefore, the indication 84 is provided to show that there is a measured length of the bale which is likely within an out of range moisture condition. Accordingly, when this bale is moved for storage, it could be a selected candidate for placement on an exterior edge of a stacked arrangement of bales, or at some other storage location where the bale is exposed to good ventilation.

Figure 10:
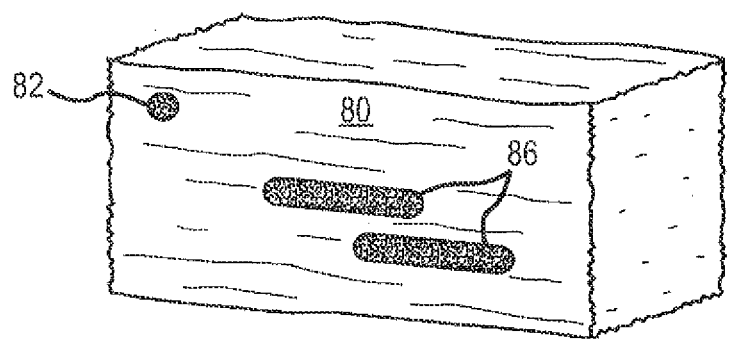
FIG. 10 provides yet another example how a bale may be marked according to the invention.

Referring to FIG. 10, another example is shown as to how a particular bale 80 may be marked according to yet another scenario. In this example, the bale includes a spot indication 82 and another type of extended or continuous indication marker 86. The indication marker 86 here is intended to show that the bale has been marked with a different type of indicator, both as to location and/or color on the bale. This different marking scheme in FIG. 10 may correspond to other measured parameters of the bale, such as the location where a selected amount of an inoculant was applied, or some other measured parameter of a moisture indication.

For each of the different marking patterns or locations where marking is applied to the bales shown in the examples of FIGS. 8-10, it should be understood that different colors can be applied to also further indicate a particular condition of the bale that is marked. One scenario in which different colors could be applied is to indicate different measured moisture ranges. For example, measured moisture at 18-20% could be marked in blue or green indicating the bale is in an acceptable moisture range. Measured moisture at 20-24% could be could be marked in yellow indicating the bale is in a less than optimal moisture range, and measured moisture at higher than 25% could be could be marked in red indicating the bale is in an out of range moisture condition. Depending upon the type of material and predetermined optimal moisture conditions considering a number of factors such as the environmental conditions and how the forage material will be stored, the particular selected moisture ranges can be varied for purposes of selectively marking bales with colors that convey the desired message.

Figure 11:
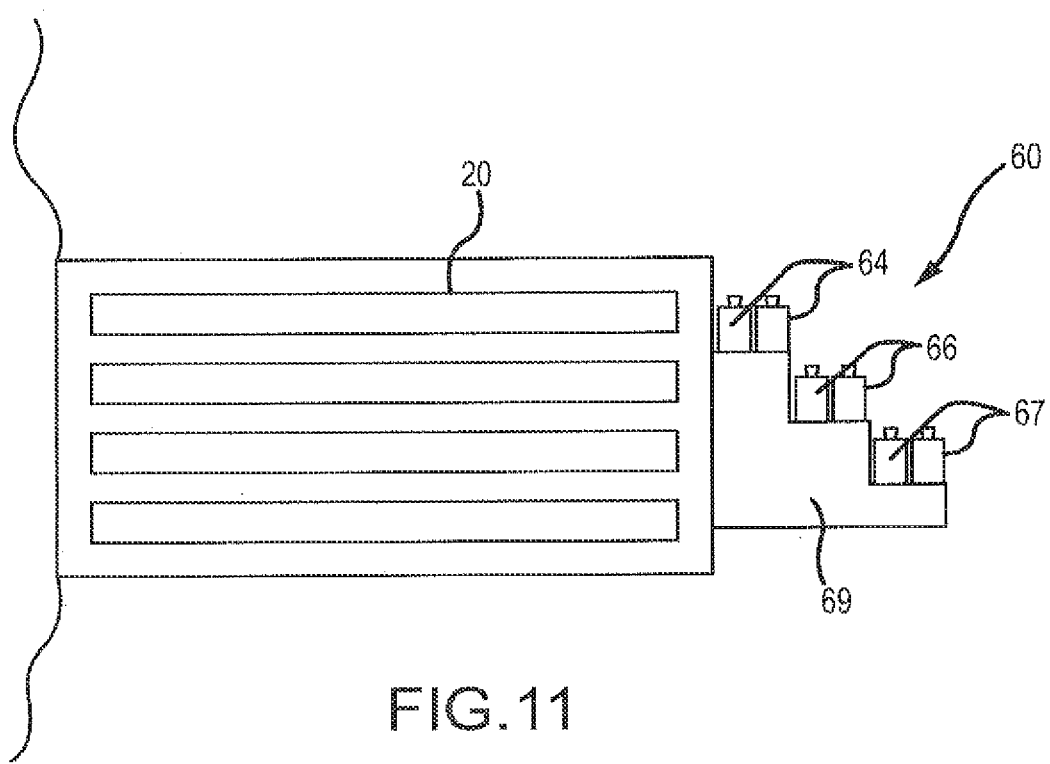
FIG. 11 is a side view of a marking station in which multiple marking applicators are provided to enable an operator to selectively create multiple types of markings on a bale of material and at different selected locations on the bale.

Referring to FIG. 11, a side view of a marking station 60 is shown according to another preferred embodiment, in which multiple marking applicators are provided to enable an operator to selectively create multiple types of markings on a bale of material at different locations on the bale. As shown, the marking station 60 includes three pairs of marking applicators 64, 66, and 67, each located at a different height application zone. The pairs of applicators are supported at their corresponding heights by a frame 69 with a plurality of stepped areas where the applicators can be mounted. The frame 69 is attached to the end of the bale chute 20. As a bale passes the marking station from the bale chute, an applicator at each application zone can selectively and independently mark the bale with indentifying information at separate height locations on the bale. Providing a pair of applicators at each application zone extends the operating life of each zone. That is, when one applicator is empty, the other applicator in the zone can be activated without having to cease bale making operations to change out an empty applicator. FIG. 10 shows three distinct locations where markings can be applied according to the marking station of FIG. 11 that has three separate application zones. The marking station of FIG. 11 can be incorporated on both sides of the baling machine; therefore, this example would include a total of twelve separate marking applicators, six on each side, and two applicators per zone.

FIG. 11 illustrates an effective yet simple marking station arrangement providing the ability to selectively mark a bale at multiple locations with different identifying information. Although three marking zones are shown, more or fewer marking zones can be adopted to match the particular marking requirements for the baled forage material.

From review of FIGS. 8-11, it should be apparent that marking a bales according to the present invention is contemplated both with respect to general spot locations for out of range moisture conditions, but also extended areas of out of range moisture conditions within a single bale. Further, marking of the bales may include markings located at different locations on the bale, markings of different colors, or markings applied in different patterns by use of selected types of spray heads attached to various different spray applicators at the marking station. The spray patterns may further be applied in letter or number forms to indicate other written or numerical codes which may correspond to pre-designated conditions of the bales by convention set for such conditions.

Figure 12:
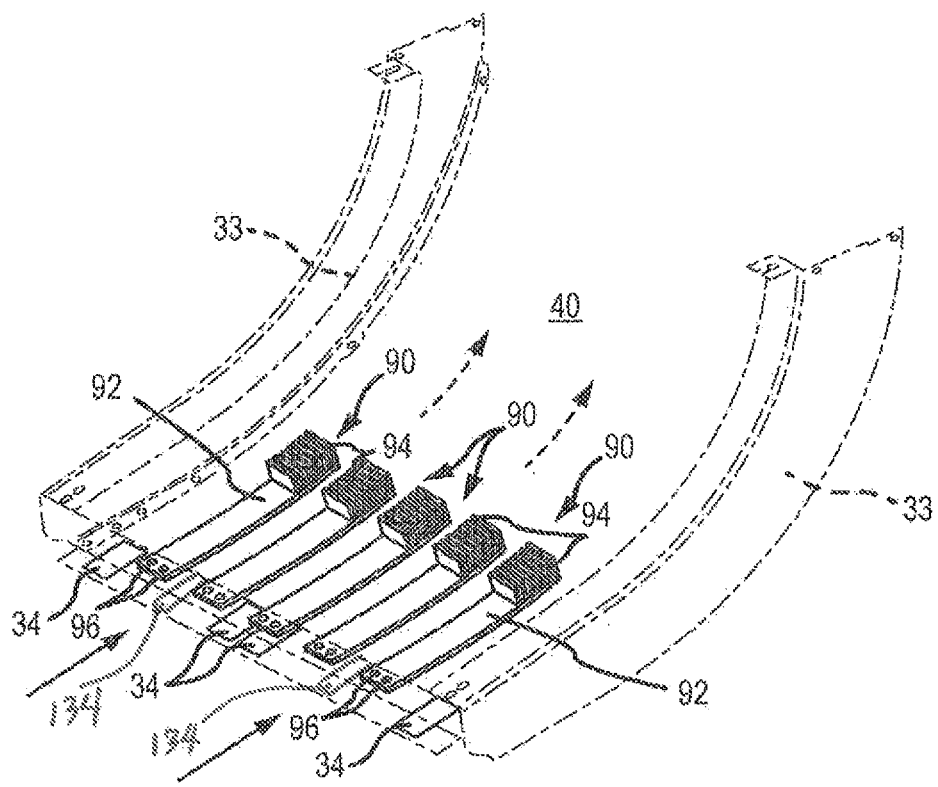
FIG. 12 illustrates a perspective view of another example of an intake area for a baling machine further including a plurality of pressure applying elements used to apply selected pressure to forage material passing over parameter sensors on a packing pan at the intake area.

FIG. 12 illustrates a perspective view of another example of an intake area for a baling machine further including a plurality of pressure applying elements or pressure fingers 90 used to apply pressure to forage material passing over moisture sensors on a packing pan at the intake area. The pressure fingers 90 are intended to provide greater consistency for pressure of the forage material applied against contact type moisture sensors 34 that may be employed for moisture sensing. These types of sensors 34, as discussed, may include conductive strips that provide a variable voltage signal back to the controller based upon measured conductivity. Measured conductivity can be influenced by the volume of material in physical contact with the sensors. If an inadequate amount of forage material passes the sensors, the sensors may not be able to detect accurate moisture content because there is not enough physical contact with the passing forage material to generate an accurate conductive signal. The pressure fingers 90 are therefore intended to ensure that lower volumes or amounts of forage material entering the intake area still make adequate physical contact with the sensors so the sensors can convey accurate signals regarding measured conductivity. The pressure fingers 90 are not intended to materially disrupt or block the flow of forage material into the machine, and rather are intended to just slightly depress and temporarily hold lower volumes of forage material so the sensors 34 can take more reliable readings.

Figure 13:
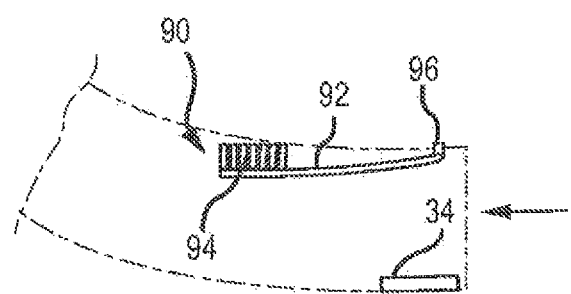
FIG. 13 is a side elevation view of a pressure applying element of FIG. 12.

The fingers 90 shown in FIGS. 12 and 13 are intended to illustrate a pressure applying element that functions similar to a leaf spring. In this regard, the fingers 90 each include a base or body 90, with one end thereof anchored at the intake opening by hardware, such as bolts or screws 96. The free hanging end of the body 90 may include a plurality of weights 94 that determine the relative ease or difficulty in which the fingers will float or ride against the upper surface of forage material. The fingers 90 are oriented within the intake opening to slightly compress the forage material but to avoid unduly trapping and holding the forage material as it passes through the intake opening. Weight can be added or subtracted to optimize the operation of the fingers to adequately depress but not unduly disrupt the flow of forage material. Five fingers 90 are shown being evenly spaced from one another, but it shall be understood that fewer than five or more than five can be used to control the forage material considering factors observed by an operator. For example, less dense, lighter forage material may require a greater number of fingers 90 to ensure there is adequate contact between the forage material and the sensors 34.

Figure 14:
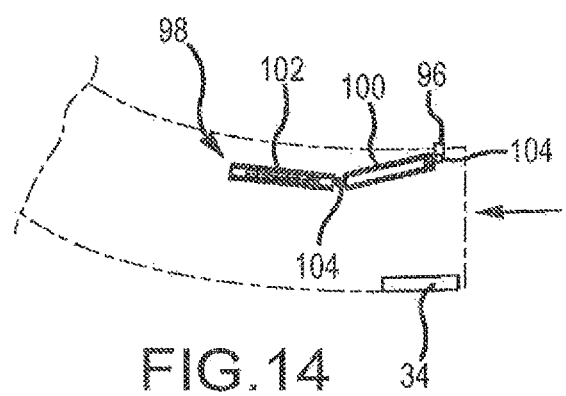
FIG. 14 is a side elevation view of another type of pressure applying element that may be adopted.

FIG. 14 is a side elevation view of another type of pressure applying element 98 that may be adopted. This element 98 has two floating pieces or parts 100 and 102. One part 100 is connected to the anchoring hardware 96 by hinge 104. The other part 102 is connected to the free end of part 100 by another hinge 104. Accordingly, parts 100 and 102 can independently float or ride against forage material as it passes through the intake opening. Optionally, weight can be added to one or both of the parts 100 and 102 to vary the amount of pressure applied. As shown, part 102 has some weight added.

According to a preferred embodiment of a method of the invention, marking of baled forage material is provided in which markings are capable of being applied to reflect various recorded parameters or characteristics of the baled forage material. In a first aspect of the method, the bales may be marked with indication regarding moisture content in which selected portions of the bale are marked corresponding to moisture content as determined when the forage material first enters the baling machine at the intake area. Various sensors are capable of accurately tracking the progression of portions of the forage material as they pass through the baling machine in which each flake within the baling chamber and bale chute can be linearly tracked such that markings can be applied, if desired, according to each flake that is ultimately bound within a single bale. In another aspect of the method, another marking that may be applied is one which reflects an amount and/or type of inoculant that may be applied to the forage material. This may be an additional marking to the bales in which both moisture content and applied inoculant can be made visible to the user. Other markings that may be applied in accordance with other aspects of the invention may include markings which reflect a particular location where forage material was obtained, a type of forage material, a date stamp when the forage material was harvested, among others. These additional markings may be placed at different locations upon the bale, in different colors, according to different designs or codes that may be placed on the bale.

To achieve selective marking of the bales, a marking station is provided in which multiple marking devices can be employed, such as a plurality of spray paint applicators that are individually controlled by commands from a controller which receives and records data regarding measured parameters, and generates outputs to the marking devices in order to selectively and controllably mark the bales.

Further in accordance with the method, a first optical sensor or proximity sensor station may be located at the intake area of the baling machine to confirm the presence or absence of forage material entering the baling machine, such as picked up from a windrow, and this first sensor may also determine an approximate amount or volume of forage material entering the machine. Also co-located at the intake area are selected moisture measurement sensors which provide an input to the controller as indications of moisture content. Inputs to the controller can be generated at selected time intervals such that each flake which is ultimately formed in the baling chamber may have a recorded moisture content measurement.

A second optical or proximity sensor station is located at the star wheel of the baling machine which serves as a mechanical timing device to determine the general location of baled material as it exits the baling chamber into the bale chute. At this location, the second optical sensor station includes, in a preferred embodiment, a pair of proximity sensors which are positioned close to the tines or spokes of the star wheel. The proximity sensors are spaced from one another corresponding to locations that enable the sensors to detect the progressive rotation of the star wheel tines. In one convention, in order to determine and confirm an incremental measured amount of forward movement of the baled material, the spaced proximity sensors must first simultaneously observe a single tine/spoke and a single space. Next, the proximity sensors must observe a single tine/spoke and a single between tines/spokes, but the observed tine/spoke in the second reading being observed by the other sensor indicating a rotation in the forward direction. If the proximity sensors detect reverse movement in which the single tine/spoke is observed to rotate in the rearward direction, this signal is noted by the controller as not corresponding to forward direction movement, but rather, is detected as rearward movement of the baled material, such as may be caused by temporary expansion of the forage material as the plunger is retracted within the baling chamber. Additionally, external vibrations or movement of the baling machine itself may result in a temporary rearward movement of the bale material, in which case, the pair of proximity sensors is also able to detect any incremental rearward movement. The signals sent from the pair of proximity sensors at the star wheel are manipulated by the controller to confirm the location of each flake as it passes through the machine.

A third proximity or optical sensor station is located at the needle assembly, and this third station is used to determine when the needle assembly is rotated to penetrate the forage material within the baling chamber for purposes of separating adjacent bales. Here, the sensor detects movement of the needle assembly each time the needle assembly is activated in its rotational or arced path of movement. Again, the controller receives inputs from this sensor station in order to determine the location of each flake that has been passed through the machine so that the marking station may precisely and accurately apply selected markings to the bale. As the needle assembly penetrates the forage material, there is some amount of separation that occurs in the material thereby creating a gap between portions of the material. This gap that is created affects the location of the forage material as it passes into the bale chute. Accordingly, this shifting of the forage material must be accounted for in order to ensure that the marking station is able to accurately dispense markings to the correct portions of each bale.

According to yet further aspects of the invention, measurement of moisture content and relative humidity may be supplemented with measurement of other parameters to further optimize application of inoculants and marking of the bales. As mentioned, these other parameters may include forage material density, volume, and temperature. Yet another observation that can be taken is to determine the nutrition value of the forage material, and to the extent the observations are quantified, this observation can also be characterized as a measured parameter.

Referring to FIGS. 3 and 12, additional sets of sensors 134, 136, and 138 are depicted, and these may correspond to sensors associated with gathering data for the other parameters to be measured including the density, volume, temperature, and/or nutritional analysis. Sensor 134 represents another contact type sensor. Sensors 136 and 138 represent additional non-contact type sensors with each being separated or offset from areas adjacent the pickup area at desired distances and angular orientations. For sensors 138, these are illustrated as being positioned in front of the pickup reel 26. The position of the sensors 138 may be better suited for sensing selected parameters such as density, volume, and/or temperature in which the sensors can be optimally spaced the desired distances from the forage material. There is presumably less room for spacing the non-contact sensors 36 and 136 that are located within the machine, and some sensors such as ultrasound sensors may require a greater offset distance from the target object.

Any one of these additional measured parameters and selected combinations thereof may be incorporated within the invention. Each type of sensor independently communicates with the controller to provide an input to the controller. The measurement of each of these parameters as measured and manipulated by the controller may result in additional user outputs in the form of user interfaces so that a user may observe and record the measured parameters. Yet further, to the extent any one of these additional measured parameters requires an adjustment of inoculants application, the control will automatically take into consideration the additional inputs and make appropriate modifications to signals generated by the controller for control of the application of the inoculants.

For measurement of the volume of the forage material, this measurement will account for variances in volumes which can allow for further adjusting the rate of inoculants applied. One preferred method of measuring this parameter is by an ultrasonic sensor represented by sensor 136 shown in FIGS. 3. This sensor is positioned at the intake area or in front of the intake area just prior to the forage material entering the baling machine. Ultrasonic sensors are typically designed for non-contact distance measurement. The ultrasonic sensor has a transceiver which transmits ultrasonic sound wave and then receives the bounce-back sound wave. The flight time of the sound waves from the sensor to the detected object(s) is measured. The ultrasonic sensors are separated from the intake area a sufficient distance so that the flight time can be measured within the sensors tolerances. Forage material with a greater volume will extend closer to the ultrasonic sensor and therefore, recorded measurements of the flight time are less for forage material of greater volume.

For measurement of the temperature of the forage material, this measurement will account for variances in temperatures which can further allow for adjusting the rate of inoculants applied. One preferred method of measuring this parameter is by use of a non-contact sensor, and this sensor may also be represented by sensor 136 as depicted in FIG. 3. One preferred method of measuring the temperature is by a thermal imaging sensor that is positioned at the intake area or in front of the intake area just prior to the forage material entering the baling machine. The thermal imaging sensor detects distinctions or differences between infrared radiation emitted by the forging material. The detected infrared radiation is provided to the controller as an input in order to record temperature of the forage material, and to therefore adjust the amount/rate of inoculants applied. For example, forage material that has a relatively high temperature may contribute to undesirable growth of fungus and bacteria, and may also contribute to a potentially catastrophic spontaneous combustion event. Accordingly, an increased amount of inoculants applied may be appropriate.

Yet another measured parameter that can be used as an input to the controller in order to further optimize application of inoculants includes the density of the forage material as it is picked up. For density, one preferred method of measuring the density is by a microwave sensor or meter that is positioned at the intake area or in front of the intake area just prior to the forage material entering the baling machine. Microwave density sensors/meters may be either contact or non-contact type; therefore, sensors 134 and 136 may represent microwave sensors/meters of the present invention. Forage material with a relatively high density may require greater amounts of applied inoculants.

Yet another measurement that can be taken, which may not necessarily be an input to the controller as mentioned, is measurements taken to determine the nutritional value of the forage material. One method of conducting this type of analysis is to take images of the forage material as it is picked up into the baling machine to determine nutritional analysis. One preferred method of conducting the nutritional analysis is by imaging of the forage material by near infrared (NIR) sensors that generate images in this wavelength, and the preferred technology for the invention may be generally referred to as NIR spectroscopy. The sensors associated for use with this method are represented by sensors 134, 136, 138, and combinations of these sensors. The nutritional content of the forage material can be analyzed and then marked on the bales of forage material. For example, FT-NIR spectroscopy can be used in which a number of different nutritional components can be measured including protein and starch content. The content of these components can be marked on the bales. Pricing and sorting of the bales can therefore be undertaken immediately after baling since the bales are already marked with desired quality indicators.

As should be apparent from review the following description and illustrations of the invention, an effective device and method are provided for tracking and marking baled forage material within a baling machine that measures any one or selected combinations of measured parameters. The device and method incorporate the use of multiple sensor stations which are used as inputs to a controller in order to record and track the location of each flake of forage material as it is collected within the baling chamber, and as each flake of the material is then compressed and transported through the machine. A marking station located at the exit of the bale chute receives commands from the controller to selectively and controllably mark each bale with predetermined markings corresponding to measured or observed parameters. The controller can be programmed to generate output signals to the marking station to reflect desired markings for specific ranges of moisture content, out of range moisture content (either too high or too low), or other moisture conditions that may be observed and recorded. Similarly, the controller can be programmed to generate output signals for marking of the bales for other measured parameters such as specific ranges, preferred ranges or values, or out of range measurements for volume, temperature, density, and nutritional content. Yet other markings may be applied to the bale corresponding to other measured parameters, such as the amount/type of inoculants applied to condition the baled forage material, and others.

While the invention is described above with respect to various preferred embodiments and attributes corresponding to each of the preferred embodiments, it shall be understood that various changes and modifications to the invention are contemplated commensurate with the scope of the claims appended hereto.

What is claimed is:

1. A device for tracking and marking baled forage material, comprising:
   a sensor station configured to determine incremental linear movement of the forage material within a baling chamber of a baling machine and movement of the forage material as it passes from the baling chamber through a bale chute of the baling machine;
   a plurality of sensors located near an intake area of the baling machine that receives the forage material, said sensors including at least one of a moisture sensor, an ultrasonic sensor for volume measurement of the forage material, a thermal imaging sensor for temperature measurement of the forage material, a microwave density sensor for density measurement of the forage material, and an NIR sensor for nutrition analysis to determine selected nutritional components of the forage material;
   a controller configured to receive input signals from the sensor station and the plurality of sensors to determine (1) the incremental linear advancement of discrete portions of the forage material as they pass through the baling machine and (2) to determine measured parameters from the input signals from the plurality of sensors, and wherein said controller is configured to transmit control signals for purposes of marking bales with an indication of the measured parameters of the forage material including at least of one of moisture content, temperature, density and nutritional components; and
   a marking station for configured to mark the bales as they have passed through the baling machine, said marking station creating marks on the bales in response to control signals transmitted from the controller indicative of at least one of the measured parameters.

2. The device, as claimed in claim 1, wherein:
   said marking station is located at an exit area of said baling machine where bales are dispensed, and said marking station includes a plurality of marking applicators for applying markings to selected bales at selected locations, with selected types of markings as determined by said controller.

3. The device, as claimed in claim 1, wherein:
   said marks created by said marking station includes at least an indication of one of said measured parameters selected portions of selected bales, said selected portions including individual flakes formed in said bale, wherein said one of said measured parameters varies between flakes in said bale, and said marks include a plurality of different marks corresponding to said one of said measured parameters for each selected portion of said bale to be marked.

4. The device, as claimed in claim 1, wherein:
   said marks created by said marking station includes at least an indication of one of said measured parameters for each selected bale, said marks being applied to corresponding locations on the bales where said one of said measured parameters was measured for the selected bales.

5. The device, as claimed in claim 1, wherein:
   said marks created by said marking station includes at least an indication of conditioning inoculants applied to a selected bale.

6. The device, as claimed in claim 1, wherein:
   said marking station is located at an exit area of said baling machine where bales are dispensed, and said marking station includes a plurality of applicator zones with at least one applicator device in each zone for applying markings to selected bales at selected locations, and selected types of markings being applied as determined by said controller that communicates with each applicator device.

7. A system for tracking and marking baled forage material, comprising:
   a linear movement sensor station configured to determine linear movement of the forage material within a baling chamber of a baling machine and movement of the forage material as it passes from the baling chamber through a bale chute of the baling machine;
   a plurality of sensors located near an intake area of the baling machine that receives the forage material, said sensors including at least one of a moisture sensor, an ultrasonic sensor for volume measurement of the forage material, a thermal imaging sensor for temperature measurement of the forage material, a microwave density sensor for density measurement of the forage material, and an NIR sensor for nutrition analysis to determine selected nutritional components of the forage material;
   a controller configured to receive input signals from the sensor stations and the plurality of sensors to determine (1) the incremental linear advancement of discrete portions of the forage material as they pass through the baling machine and (2) to determine measured parameters from the input signals from the plurality of sensors, and wherein said controller is configured to transmit control signals for purposes of marking bales with an indication of the measured parameters of the forage material including at least of one of moisture content, temperature, density and nutritional components; and a marking station configured to mark the bales as they have passed through the baling machine, said marking station creating marks on the bales in response to control signals transmitted from the controller indicative of at least one of the measured parameters.

8. The system, as claimed in claim 7, wherein:

said marking station is located at an exit area of said baling machine where bales are dispensed, and said marking station includes a plurality of marking applicators for applying markings to selected bales at selected locations, with selected types of markings as determined by said controller.

9. The system, as claimed in claim 7, wherein:

said marks created by said marking station includes at least an indication of one of said measured parameters for each selected bale, said marks being applied to corresponding locations on the bales where the measured parameter was measured for the selected bales.

10. The system, as claimed in claim 7, wherein:

said marks created by said marking station includes at least an indication of one of said measured parameters for selected portions of selected bales, said selected portions including individual flakes formed in said bale, wherein said one of said measure parameters varies between flakes in said bale, and said marks include a plurality of different marks corresponding to said of one said measured parameters for each selected portion of said bale to be marked.

11. The system, as claimed in claim 7, wherein:

said marking station is located at an exit area of said baling machine where bales are dispensed, and said marking station includes a plurality of applicator zones with at least one applicator device in each zone for applying markings to selected bales at selected locations, and selected types of markings being applied as determined by said controller that communicates with each applicator device.

12. A method for tracking and marking baled forage material, comprising:

determining linear movement of the forage material within a baling chamber of a baling machine and movement of the forage material as it passes from the baling chamber through a bale chute of the baling machine by a linear movement sensor station;

determining and tracking respective locations of portions of the forage material by a controller as the forage material passes through the baling machine, wherein each of the portions has at least one corresponding measured parameter as measured by a corresponding parameter sensor communicating with the controller;

receiving input signals by the controller from the sensor station reflective of relative positional changes of the forage material passing through the baling machine;

receiving further input signals by the controller from the parameter sensors;

transmitting bale marking commands from said controller to a marking station for marking bales, said bale marking commands being transmitted for purposes of marking bales with an indication of at least one of the measured parameters of the forage material including at least one of moisture content, volume, temperature, density, and nutrition content; and marking the bales by the marking station in which marks are created in response to the bale marking commands transmitted from the controller indicative of at least one of the measured parameters for corresponding portions of the bales.

13. The method, as claimed in claim 12, wherein:

said marks created by said marking station includes at least an indication of moisture content for each selected bale, said marks being applied to corresponding locations on the bales where the moisture content was measured for the selected bales.

14. The method, as claimed in claim 12, wherein:

said parameter sensor includes at least one of a moisture sensor, an ultrasonic sensor for volume measurement, a thermal imaging sensor for temperature measurement, a microwave density sensor for density measurement, and an NIR sensor for nutrition analysis to determine selected nutritional components.

* * * * *

UNITED STATES PATENT AND TRADEMARK OFFICE
CERTIFICATE OF CORRECTION

Page 1 of 1

PATENT NO. : 10,542,679 B2
APPLICATION NO. : 15/784932
DATED : January 28, 2020
INVENTOR(S) : Bill Younk and Wes Byers It is certified that error appears in the above-identified patent and that said Letters Patent is hereby corrected as shown below:

In the Claims

Column 22, Line 5, delete "for".

Signed and Sealed this
Thirty-first Day of March, 2020

Andrei Iancu
*Director of the United States Patent and Trademark Office*